(12) United States Patent
Mizrachi Nebenzahl

(10) Patent No.: US 7,504,110 B2
(45) Date of Patent: Mar. 17, 2009

(54) **PROTEIN-BASED *STREPTOCOCCUS PNEUMONIAE* VACCINES**

(75) Inventor: Yaffa Mizrachi Nebenzahl, Beer Sheva (IL)

(73) Assignee: Ben-Gurion University of the Negev Research and Development Authority, Beer-Sheva (IL)

( * ) Notice: Subject to any disclaimer, the term of this patent is extended or adjusted under 35 U.S.C. 154(b) by 327 days.

(21) Appl. No.: 10/953,513

(22) Filed: Sep. 30, 2004

(65) Prior Publication Data

US 2005/0196415 A1 Sep. 8, 2005

Related U.S. Application Data

(63) Continuation-in-part of application No. PCT/IL03/00271, filed on Apr. 1, 2003.

(60) Provisional application No. 60/368,981, filed on Apr. 2, 2002.

(51) Int. Cl.
*A61K 39/09* (2006.01)
*A61K 39/02* (2006.01)
*A61K 39/00* (2006.01)
*A61K 39/385* (2006.01)
*A61K 38/00* (2006.01)
*C07K 1/00* (2006.01)

(52) U.S. Cl. .............. 424/244.1; 424/234.1; 424/184.1; 424/190.1; 424/193.1; 514/2; 530/300; 530/350; 530/825

(58) Field of Classification Search .............. 424/244.1, 424/234.1, 184.1, 190.1, 193.1; 514/2; 530/350, 530/300, 825
See application file for complete search history.

(56) References Cited

U.S. PATENT DOCUMENTS 5,728,387 A 3/1998 Briles et al.
6,699,703 B1 * 3/2004 Doucette-Stamm et al. ...... 435/252.3
7,078,492 B2 * 7/2006 Pirofski et al. ........... 530/387.3

FOREIGN PATENT DOCUMENTS

EP 0 899 334 3/1999

OTHER PUBLICATIONS

Jado et al. Curr. Microbiol. 39: 31-36, 1999.*
Houghten et al. Vaccines86, Cold Spring Harbor Laboratory, p. 21-25, 1986.*
Briles D. E. et al., "The potential for using protein vaccines to protect against otitis media caused by *Streptococcus pneumoniae*" Vaccine, Dec. 8, 2000; 19 Suppl 1:S87-S95.
Bethe G. et al., "The cell wall-associated serine protease PrtA: a highly conserved virulence factor of *Streptococcus pneumoniae*". FEMS Microbiol Lett. Nov. 27, 2001;205(1):99-104.
Ling et al., "Surface Lectin (L) and Non-Lectin (NL) Proteins as Novel Vaccine Candidates for *S. pneumoniae* (Pnc).", Abstracts of the Interscience Conference on Antimicrobial Agents and Chemotherapy, American Society for Microbiology, San Diego, CA, Sep. 27-30, 2002, vol. 42, p. 247, abstract.
Jedrzejas, "Pneumococcal Virulence Factors: Structure and Function", Microbiology and Molecular Biology Reviews, Jun. 2001, vol. 65, No. 2, pp. 187-207.
McDaniel, "Analysis of Protection Eliciting Pneumococcal Cell Surface Components form PSPA (Pneumococcal Surface Protein A) Mutants", Abstracts of the Interscience Conference on Antimicrobial Agents and Chemotherapy, American Society for Microbiology, San Diego, CA, Sep. 27-30, 2002, p. A1257.
Lifshitz et al., "*Streptococaus pneumoniae* (Pnc) Surface Proteins: Profile of Antibody Response during Health, Disease, and Convalescence", Abstracts of the 39th Interscience Conference on Antimicrobial Agents and Chemotherapy, American Society for Microbiology, San Francisco, CA, Sep. 26-29, 1999, p. 360, abstract.

* cited by examiner

*Primary Examiner*—S. Devi
(74) *Attorney, Agent, or Firm*—Winston & Strawn LLP

(57) ABSTRACT

The present invention is primarily directed to a method for preventing infection of a mammalian subject with *S. pneumoniae*, wherein said method comprises administering to said subject an effective amount of one or more *S. pneumoniae* cell wall and/or cell membrane proteins and/or immunogenically-active fragments, derivatives or modifications thereof, wherein said proteins are selected from a defined group of immunogenic proteins. The present invention further provides vaccine compositions containing said cell wall and/or cell membrane proteins.

6 Claims, 5 Drawing Sheets

US 7,504,110 B2

PROTEIN-BASED *STREPTOCOCCUS PNEUMONIAE* VACCINES

This application is a continuation-in-part of PCT International application No. PCT/IL03/00271, filed 1 Apr. 2003, which designated the US and claims priority to U.S. Provisional Application No. 60/368,981, filed Apr. 2, 2002. The entire contents of these applications are incorporated herein by reference.

FIELD OF THE INVENTION

The present invention relates to a method for vaccinating subjects against infection with *Streptococcus pneumoniae*. More specifically, the present invention provides a vaccination method based on the use of immunogenic *S. pneumoniae* cell wall and cell membrane proteins and/or immunogenically-active fragments thereof, as well as vaccine compositions comprising said proteins and/or fragments.

BACKGROUND OF THE INVENTION

The Gram-positive bacterium *Streptococcus pneumoniae* is a major cause of disease, suffering and death worldwide. Diseases caused by infection with this agent include otitis media, pneumonia, bacteremia, meningitis and sepsis. In some cases, infected individuals may become asymptomatic carriers of *S. pneumoniae*, thereby readily allowing the rapid spread of this infective agent throughout the population. In view of the serious consequences of infection with *S. pneumoniae*, as well as its rapid spread within and between populations, there is an urgent need for safe, effective vaccination regimes.

Current methods of vaccination are based on inoculation of the subject with polysaccharides obtained from the capsules of *S. pneumoniae*. While these polysaccharide-based vaccine preparations have been found to be reasonably efficacious when used to prevent infection in adult populations, they are significantly less useful in the treatment of young children (under two years of age) and the elderly. One commonly-used capsular polysaccharide 23-valent vaccine, for example, has been found to be only 60% effective in preventing *S. pneumoniae* invasive disease in elderly subjects and completely incapable of yielding clinically-useful antibody responses in the under-two age group [Shapiro E. D. et al. (1991) N. Engl. J. Med. 325: 1453-1460].

In an attempt to increase the immunogenicity of these vaccines, various compositions comprising capsular polysaccharides that have been conjugated with various carrier or adjuvant proteins have been used. Although vaccines of this type constitute an improvement in relation to the unconjugated polysaccharide vaccines, they have not overcome the problem of coverage, since they are effective against only about 10% of the 92 known capsular serotypes. Consequently, upon vaccination, repopulation with serotypes not present in the vaccine occurs.

In the cases of certain other bacteria of pathogenic importance for human and other mammalian species, vaccines comprising immunogenic virulence proteins are currently being developed. Such protein-based vaccines should be of particular value in the case of vulnerable subjects such as very young children, in view of the fact that such subjects are able to produce antibodies against foreign proteins. Unfortunately, very little is known of the molecular details of the life cycle of *S. pneumoniae*, or of the nature of role of the various virulence factors which are known or thought to be involved in targeting and infection of susceptible hosts.

It is a purpose of the present invention to provide a method for protecting individuals against infection with *S. pneumoniae* by the use of a protein-based vaccine.

It is another purpose of the invention to provide a protein-based vaccine that is prepared from the immunogenic cell wall and/or cell membrane proteins of *S. pneumoniae*.

It is yet another purpose of the invention to provide a vaccination method that overcomes the problems and drawbacks of prior art methods.

Further objects and advantages of the present invention will become apparent as the description proceeds.

SUMMARY OF THE INVENTION

It has now been found that it is possible to protect individuals against infection with *S. pneumoniae* by means of administering to said individuals a vaccine composition comprising one or more proteins isolated from the outer layers of the aforementioned bacteria and/or one or more immunogenically-active fragments, derivatives or modifications thereof. Unexpectedly, it was found that such vaccine compositions are effective against a wide range of different *S. pneumoniae* serotypes, and in all age groups, including those age groups which do not produce anti-*S. pneumoniae* antibodies following inoculation with polysaccharide-based vaccines.

It is to be noted that in the context of the present invention, the terms "fragments", "derivatives" and "modifications" are to be understood as follows:

"Fragment": a less than full length portion of the native sequence of the protein in question, wherein the sequence of said portion is essentially unchanged as compared to the relevant part of the sequence of the native protein.

"Derivative": a less than full length portion of the native sequence of the protein in question, wherein either the sequence further comprises (at its termini and/or within said sequence itself) non-native sequences, i.e. sequences which do not form part of the native protein in question. The term "derivative" also includes within its scope molecular species produced by conjugating chemical groups to the amino acid residue side chains of the native proteins or fragments thereof, wherein said chemical groups do not form part of the naturally-occurring amino acid residues present in said native proteins.

"Modification": a full length protein or less than full length portion thereof comprising non-native amino acid residues and sequences of such non-native residues, which have been introduced as a consequence of mutation of the native sequence (by either random or site-directed processes).

The term "immunogenically-active" is used herein in ordinary sense to refer to an entity (such as a protein or its fragment or derivative) that is capable of eliciting an immune response when introduced into a host subject.

The present invention is primarily directed to a method for preventing infection of mammalian subjects with *S. pneumoniae*, wherein said method comprises administering to a subject in need of such treatment an effective amount of one or more *S. pneumoniae* cell wall and/or cell membrane proteins and/or immunogenically-active fragments, derivatives or modifications thereof, wherein said proteins are selected from the group consisting of: phosphoenolpyruvate protein phosphotransferase, phospho-mannomutase, trigger factor, elongation factor G, tetracycline resistance protein (tetO), DNA directed RNA polymerase alpha-chain, NADH oxidase, glutamyl-tRNA amidotransferase subunit A, N utilization substance protein A homolog, XAA-HIS dipeptidase, cell division protein ftsz, zinc metalloproteinase in SCAA 5' region (ORF 6), L-lactate dehydrogenase, glyceraldehyde 3-phosphate dehydrogenase (GAPDH), fructose-biphosphate aldolase, UDP-glucose 4-epimerase, GTP binding protein typA/BipA, GMP synthase, glutamyl-tRNA synthetase, NADP-specific glutamate dehydrogenase, Elongation factor TS, phosphoglycerate kinase (cell wall protein), pyridine nucleotide-disulfide oxido-reductase, 40S ribosomal protein S1, 6-phosphogluconate dehydrogenase, aminopeptidase C, carbomyl-phosphate synthase (large subunit), PTS system mannose-specific IIAB components, ribosomal protein S2, dihydroorotate dehydrogenase, aspartate carbamoyltransferase, elongation factor Tu, Pneumococcal surface immunogenic protein A (PsipA), phosphoglycerate kinase (cell membrane protein), ABC transporter substrate-binding protein, endopeptidase O, Pneumococcal surface immunogenic protein B (PsipB) and Pneumococcal surface immunogenic protein C (PsipC).

The means used to identify the aforementioned S. pneumoniae proteins, and their unique public access database accession codes will be disclosed and described hereinbelow.

In a preferred embodiment of the method of the present invention, one or more adjuvants may be optionally administered to the subject together with one or more of the aforementioned S. pneumoniae cell wall and/or cell membrane proteins or fragments thereof.

In one particularly preferred embodiment, the method of the present invention for preventing infection of mammalian subjects by S. pneumoniae comprises administering to a subject in need of such treatment an effective amount of S. pneumoniae glyceraldehyde 3-phosphate dehydrogenase (GAPDH).

In another particularly preferred embodiment, the method of the present invention for preventing infection of mammalian subjects by S. pneumoniae comprises administering to a subject in need of such treatment an effective amount of S. pneumoniae fructose-biphosphate aldolase.

In a further particularly preferred embodiment, the method of the present invention for preventing infection of mammalian subjects by S. pneumoniae comprises administering to a subject in need of such treatment an effective amount of one or more immunogenically-active fragments of the aforementioned S. pneumoniae fructose-biphosphate aldolase protein. Although many such active fragments may be generated from this protein and used in the presently-disclosed method, in an especially preferred embodiment, the active fragment used corresponds to the peptide encoded by the first 294 nucleotides of the fructose biphosphate aldolase gene (SP0605 Streptococcus pneumoniae TIGR4), referred to herein as SEQ ID no.1, and defined in the sequence listing that forms an integral part of the present disclosure.

In one preferred embodiment of the method of the invention, the cell wall and/or cell membrane proteins are S. pneumoniae proteins that are associated with an age-related immune response.

The term "age-related immune response" (as used throughout this application) indicates that the ability of subjects to produce antibodies to the protein or proteins causing said immune response increases with age. In the case of human subjects, said ability is measured over a time scale beginning with neonates and ending at approximately age four years and adults. In non-human mammalian subjects, the "age-related immune response" is measured over an age range extending from neonates to an age at which the immune system of the young mammal is at a stage of development comparable to that of a pre-puberty human child and adults.

In another preferred embodiment of the method of the invention, the cell wall and/or cell membrane proteins are lectins.

In another preferred embodiment of the method of the invention, the cell wall and/or cell membrane proteins are non-lectins.

In another preferred embodiment of the method of the invention, the cell wall and/or cell membrane proteins are a mixture of lectins and non-lectins.

The term "lectins" is used hereinabove and hereinbelow to indicate proteins having the ability to specifically bind to polysaccharides or oligosaccharides. Conversely, the term "non-lectins" is used to refer to proteins lacking the aforementioned saccharide-binding property.

In one preferred embodiment of the method of the invention, the mammalian subject is a human subject.

In another aspect, the present invention is directed to a vaccine composition comprising as the active ingredient one or more S. pneumoniae cell wall and/or cell membrane proteins and/or immunogenically-active fragments, derivatives or modifications thereof, wherein said proteins are selected from the group consisting of: phosphoenolpyruvate protein phosphotransferase, phospho-mannomutase, trigger factor, elongation factor G, tetracycline resistance protein (tetO), DNA directed RNA polymerase alpha-chain, NADH oxidase, glutamyl-tRNA amidotransferase subunit A, N utilization substance protein A homolog, XAA-HIS dipeptidase, cell division protein ftsz, zinc metalloproteinase in SCAA 5' region (ORF 6), L-lactate dehydrogenase, glyceraldehyde 3-phosphate dehydrogenase (GAPDH), fructose-biphosphate aldolase, UDP-glucose 4-epimerase, GTP binding protein typA/BipA, GMP synthase, glutamyl-tRNA synthetase, NADP-specific glutamate dehydrogenase, Elongation factor TS, phosphoglycerate kinase (cell wall protein), pyridine nucleotide-disulfide oxido-reductase, 40S ribosomal protein S1, 6-phosphogluconate dehydrogenase, aminopeptidase C, carbomyl-phosphate synthase (large subunit), PTS system mannose-specific IIAB components, ribosomal protein S2, dihydroorotate dehydrogenase, aspartate carbamoyltransferase, elongation factor Tu, Pneumococcal surface immunogenic protein A (PsipA), phosphoglycerate kinase (cell membrane protein), ABC transporter substrate-binding protein and endopeptidase O, Pneumococcal surface immunogenic protein B (PsipB) and Pneumococcal surface immunogenic protein C (PsipC).

The vaccine compositions of the present invention may also contain other, non-immunologically-specific additives, diluents and excipients. For example, in many cases, the vaccine compositions of the present invention may contain—in addition to the S. pneumoniae cell-wall and/or cell-membrane protein(s)—one or more adjuvants.

In one particularly preferred embodiment, the vaccine composition of the present invention comprises an effective amount of S. pneumoniae glyceraldehyde 3-phosphate dehydrogenase (GAPDH) as the active ingredient.

In another particularly preferred embodiment of the present invention, the vaccine composition comprises an effective amount of S. pneumoniae fructose-biphosphate aldolase as the active ingredient.

In a further particularly preferred embodiment, the vaccine composition of the present invention for preventing infection of mammalian subjects by S. pneumoniae comprises an effective amount of one or more immunogenically-active fragments of the aforementioned S. pneumoniae fructose-biphosphate aldolase protein. Although many such active fragments may be generated from this protein and incorporated into the presently-disclosed composition, in an especially preferred embodiment, the active fragment used corresponds to the peptide encoded by the first 294 nucleotides of the fructose biphosphate aldolase gene (SP0605 Streptococcus pneumoniae TIGR4), herein referred to as SEQ ID no.1.

The aforementioned vaccine compositions may clearly be used for preventing infection of the mammalian subjects by S. pneumoniae. However, said vaccine composition is not restricted to this use alone. Rather it may be usefully employed to prevent infection by any infectious agent whose viability or proliferation may be inhibited by the antibodies generated by a host in response to the inoculation therein of the one or more S. pneumoniae proteins provided in said composition.

In one preferred embodiment of the vaccine composition of the present invention, the cell wall and/or cell membrane proteins are *S. pneumoniae* proteins that are associated with an age-related immune response.

In another preferred embodiment of the vaccine composition of the present invention, the cell wall and/or cell membrane proteins are lectins.

In another preferred embodiment of the vaccine composition of the present invention, the cell wall and/or cell membrane proteins are non-lectins.

In a further preferred embodiment of the vaccine composition of the present invention, the cell wall and/or cell membrane proteins are a mixture of lectins and non-lectins.

The present invention also encompasses the use of one or more *S. pneumoniae* cell wall and/or cell membrane proteins and/or immunogenically-active fragments, derivatives or modifications thereof in the preparation of a vaccine for use in the prevention of diseases and carrier states caused by said *S pneumoniae*, wherein said proteins are selected from the group consisting of: phosphoenolpyruvate protein phosphotransferase, phospho-mannomutase, trigger factor, elongation factor G, tetracycline resistance protein (tetO), DNA directed RNA polymerase alpha-chain, NADH oxidase, glutamyl-tRNA amidotransferase subunit A, N utilization substance protein A homolog, XAA-HIS dipeptidase, cell division protein ftsz, zinc metalloproteinase in SCAA 5' region (ORF 6), L-lactate dehydrogenase, glyceraldehyde 3-phosphate dehydrogenase (GAPDH), fructose-biphosphate aldolase, UDP-glucose 4-epimerase, GTP binding protein typA/BipA, GMP synthase, glutamyl-tRNA synthetase, NADP-specific glutamate dehydrogenase, Elongation factor TS, phosphoglycerate kinase (cell wall protein), pyridine nucleotide-disulfide oxido-reductase, 40S ribosomal protein S1, 6-phosphogluconate dehydrogenase, aminopeptidase C, carbomyl-phosphate synthase (large subunit), PTS system mannose-specific IIAB components, ribosomal protein S2, dihydroorotate dehydrogenase, aspartate carbamoyltransferase, elongation factor Tu, Pneumococcal surface immunogenic protein A (PsipA), phosphoglycerate kinase (cell membrane protein), ABC transporter substrate-binding protein endopeptidase O, Pneumococcal surface immunogenic protein B (PsipB) and Pneumococcal surface immunogenic protein C (PsipC).

In one particularly preferred embodiment, the protein used in the preparation of the vaccine is *S. pneumoniae* glyceraldehyde 3-phosphate dehydrogenase (GAPDH).

In another particularly preferred embodiment of the present invention, the protein used in the preparation of the vaccine is *S. pneumoniae* fructose-biphosphate aldolase.

In a further particularly preferred embodiment of this aspect of the present invention, an immunogenically-active fragment of the aforementioned *S. pneumoniae* fructose-biphosphate aldolase protein is used in the preparation of the vaccine. Although many such active fragments may be generated from this protein and used in the preparation of the vaccine, in an especially preferred embodiment, the active fragment used corresponds to the peptide encoded by the first 294 nucleotides of the fructose biphosphate aldolase gene (SP0605 *Streptococcus pneumoniae* TIGR4), herein referred to as SEQ ID no.1.

Preferably, the cell wall and/or cell membrane proteins used in the preparation of said vaccine are *S. pneumoniae* proteins that are associated with an age-related immune response.

In another preferred embodiment, the cell wall and/or cell membrane proteins used in the preparation of the abovementioned vaccine are lectins.

In yet another preferred embodiment the cell wall and/or cell membrane proteins used in the preparation of the abovementioned vaccine are non-lectins.

In a further preferred embodiment, the cell wall and/or cell membrane proteins used in the preparation of the abovementioned vaccine are a mixture of lectins and non-lectins.

The present invention is also directed to one or more *S. pneumoniae* cell wall and/or cell membrane proteins and/or immunogenically-active fragments, derivatives or modifications thereof for use as a vaccine for the prevention of diseases and carrier states caused by said *S pneumoniae*, wherein said proteins are selected from the group consisting of: phosphoenolpyruvate protein phosphotransferase, phospho-mannomutase, trigger factor, elongation factor G, tetracycline resistance protein (tetO), DNA directed RNA polymerase alpha-chain, NADH oxidase, glutamyl-tRNA amidotransferase subunit A, N utilization substance protein A homolog, XAA-HIS dipeptidase, cell division protein ftsz, zinc metalloproteinase in SCAA 5' region (ORF 6), L-lactate dehydrogenase, glyceraldehyde 3-phosphate dehydrogenase (GAPDH), fructose-biphosphate aldolase, UDP-glucose 4-epimerase, GTP binding protein typA/BipA, GMP synthase, glutamyl-tRNA synthetase, NADP-specific glutamate dehydrogenase, Elongation factor TS, phosphoglycerate kinase (cell wall protein), pyridine nucleotide-disulfide oxido-reductase, 40S ribosomal protein S1, 6-phosphogluconate dehydrogenase, aminopeptidase C, carbomyl-phosphate synthase (large subunit), PTS system mannose-specific IIAB components, ribosomal protein S2, dihydroorotate dehydrogenase, aspartate carbamoyltransferase, elongation factor Tu, Pneumococcal surface immunogenic protein A (PsipA), phosphoglycerate kinase (cell membrane protein), ABC transporter substrate-binding protein, endopeptidase O, Pneumococcal surface immunogenic protein B (PsipB) and Pneumococcal surface immunogenic protein C (PsipC).

In one particularly preferred embodiment, the protein for use as said vaccine is *S. pneumoniae* glyceraldehyde 3-phosphate dehydrogenase (GAPDH).

In another particularly preferred embodiment of the present invention, the protein for use as said vaccine is *S. pneumoniae* fructose-biphosphate aldolase.

In a further particularly preferred embodiment of this aspect of the present invention, an immunogenically-active fragment of the aforementioned *S. pneumoniae* fructose-biphosphate aldolase protein is provided for use as said vaccine. Although many such active fragments may be generated from this protein and used in the preparation of the vaccine, in an especially preferred embodiment, the active fragment used corresponds to the peptide encoded by the first 294 nucleotides of the fructose biphosphate aldolase gene (SP0605 *Streptococcus pneumoniae* TIGR4), herein referred to as SEQ ID no.1.

In one preferred embodiment, the cell wall and/or cell membrane proteins for use as described above are *S. pneumoniae* proteins associated with an age-related immune response.

In another preferred embodiment, the aforementioned cell wall and/or cell membrane proteins are lectins.

In a further preferred embodiment, the aforementioned cell wall and/or cell membrane proteins are non-lectins.

In a still further preferred embodiment, the aforementioned cell wall and/or cell membrane proteins are a mixture of lectins and non-lectins.

It is to be noted that when the *S. pneumoniae* proteins and/or fragments, derivatives or modifications thereof used in the aforementioned methods, compositions and vaccines are lectins, said methods, compositions and vaccines are particularly efficacious in the prevention of localized *S. pneumoniae* infections. In one preferred embodiment, the localized infections are infections of mucosal tissue, particularly of nasal and other respiratory mucosa.

Conversely, when the *S. pneumoniae* proteins and/or their fragments, derivatives or modifications used in the aforementioned methods, compositions and vaccines are non-lectins, said methods, compositions and vaccines are particularly efficacious in the prevention of intra-peritoneal and systemic S. pneumoniae infections.

All of the above and other characteristics and advantages of the present invention will be further understood from the following illustrative and non-limiting examples of preferred embodiments thereof.

BRIEF DESCRIPTION OF THE DRAWINGS

FIG. 5 illustrates the use of the pHAT expression vector in cloning the ALDO 1 fragment of S. pneumoniae fructose biphosphate aldolase. FIG. 5A is a schematic illustration of the construction of the pHAT expression vector, while

DETAILED DESCRIPTION OF PREFERRED EMBODIMENTS

Figure 1:
FIG. 1 is a photograph of a Western blot in which the sera of mice immunized with (A) recombinant GAPDH and (B) recombinant fructose-biphosphate aldolase are seen to recognize the corresponding native proteins (CW) (in an electrophoretically-separated total cell wall protein preparation), and the corresponding recombinant protein (R).

Vaccination protects individuals (and by extension, populations) from the harmful effects of pathogenic agents, such as bacteria, by inducing a specific immunological response to said pathogenic agents in the vaccinated subject.

Vaccines are generally, but not exclusively, administered by means of injection, generally by way of the intramuscular, intradermal or subcutaneous routes. Some vaccines may also be administered by the intravenous, intraperitoneal, nasal or oral routes.

The S. pneumoniae-protein containing preparations of the invention can be administered as either single or multiple doses of an effective amount of said protein. The term "effective amount" is used herein to indicate that the vaccine is administered in an amount sufficient to induce or boost a specific immune response, such that measurable amounts (or an increase in the measurable amounts) of one or more antibodies directed against the S. pneumoniae proteins used may be detected in the serum or plasma of the vaccinated subject. The precise weight of protein or proteins that constitutes an "effective amount" will depend upon many factors including the age, weight and physical condition of the subject to be vaccinated. The precise quantity also depends upon the capacity of the subject's immune system to produce antibodies, and the degree of protection desired. Effective dosages can be readily established by one of ordinary skill in the art through routine trials establishing dose response curves. However, for the purposes of the present invention, effective amounts of the compositions of the invention can vary from 0.01-1,000 µg/ml per dose, more preferably 0.1-500 µg/ml per dose, wherein the usual dose size is 1 ml.

The vaccines of the present invention will generally comprise an effective amount of one or more S. pneumoniae proteins as the active component, suspended in an appropriate vehicle. In the case of intranasal formulations, for example, said formulations may include vehicles that neither cause irritation to the nasal mucosa nor significantly disturb ciliary function. Diluents such as water, aqueous saline may also be added. The nasal formulations may also contain preservatives including, but not limited to, chlorobutanol and benzalkonium chloride. A surfactant may be present to enhance absorption of the subject proteins by the nasal mucosa. An additional mode of antigen delivery may include an encapsulation technique, which involves complex coacervation of gelatin and chondroitin sulfate (Azhari R, Leong K W. 1991. Complex coacervation of chondroitin sulfate and gelatin and its use for encapsulation and slow release of a model protein. Proc. Symp. Control. Rel. 18:617; Brown K E, Leong K, Huang C H, Dalal R, Green G D, Haimes H B, Jimenez P A, Bathon J. 1998. Gelatin/chondroitin 6-sulfate microspheres for delivery of therapeutic proteins to the joint. Arthritis Rheum 41:2185-2195).

The present invention also encompasses within its scope the preparation and use of DNA vaccines. Vaccination methods and compositions of this type are well known in the art and are comprehensively described in many different articles, monographs and books (see, for example, chapter 11 of "Molecular Biotechnology: principles and applications of recombinant DNA" eds. B. R. Glick & J. J. Pasternak, ASM Press, Washington, D.C., $2^{nd}$ edition, 1998). In principle, DNA vaccination is achieved by cloning the cDNAs for the desired immunogen into a suitable DNA vaccine vector, such as the pVAC vector (Invivogen). In the case of pVAC, the desired immunogenic proteins are targeted and anchored to the cell surface by cloning the gene of interest in frame between the IL2 signal sequence and the C-terminal transmembrane anchoring domain of human placental alkaline phosphatase. Such DNA vaccine vectors are specifically designed to stimulate humoral immune responses by intramuscular injection. The antigenic peptide produced on the surface of muscle cells is taken up by antigen presenting cells (APCs) and processed through the major histocompatibility complex (MHC) class II pathway.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

However, in general, the vaccines of the present invention would normally be administered parenterally, by the intramuscular, intravenous, intradermal or subcutaneous routes, either by injection or by a rapid infusion method. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Besides the abovementioned inert diluents and solvents, the vaccine compositions of the invention can also include adjuvants, wetting agents, emulsifying and suspending agents, or sweetening, flavoring, or perfuming agents.

The aforementioned adjuvants are substances that can be used to augment a specific immune response. Normally, the adjuvant and the composition are mixed prior to presentation to the immune system, or presented separately, but into the same site of the subject being vaccinated. Adjuvants that may be usefully employed in the preparation of vaccines include: oil adjuvants (for example, Freund's complete and incomplete adjuvants, that will be used in animal experiments only and is forbidden from use in humans), mineral salts, alum, silica, kaolin, and carbon, polynucleotides and certain natural substances of microbial origin. An additional mode of antigen delivery may include an encapsulation technique, which involves complex coacervation of gelatin and chondroitin sulfate (Azhari R, Leong K W. 1991. Complex coacervation of chondroitin sulfate and gelatin and its use for encapsulation and slow release of a model protein. Proc. Symp. Control. Rel. 18:617; Brown K E, Leong K, Huang C H, Dalal R, Green G D, Haimes H B, Jimenez P A, Bathon J. 1998. Gelatin/chondroitin 6-sulfate microspheres for delivery of therapeutic proteins to the joint. Arthritis Rheum 41:2185-2195).

Further examples of materials and methods useful in the preparation of vaccine compositions are well known to those skilled in the art. In addition, further details may be gleaned from Remington's Pharmaceutical Sciences, Mack Publishing Co, Easton, Pa., USA (1980).

The S. pneumoniae cell-wall and/or cell-membrane proteins for use in working the present invention may be obtained by directly purifying said proteins from cultures of S. pneumoniae by any of the standard techniques used to prepare and purify cell-surface proteins. Suitable methods are described in many biochemistry text-books, review articles and laboratory guides, including inter alia "Protein Structure: a practical approach" ed. T. E. Creighton, IRL Press, Oxford, UK (1989).

However, it is to be noted that such an approach suffers many practical limitations that present obstacles for producing commercially-viable quantities of the desired proteins. The S. pneumoniae proteins of the present invention may therefore be more conveniently prepared by means of recombinant biotechnological means, whereby the gene for the S. pneumoniae protein of interest is isolated and inserted into an appropriate expression vector system (such as a plasmid or phage), which is then introduced into a host cell that will permit large-scale production of said protein by means of, for example, overexpression.

As a first stage, the location of the genes of interest within the S. pneumoniae genome may be determined by reference to a complete-genome database such as the TIGR database that is maintained by the Institute for Genomic Research (web site: http colon double slash www dot tigr dot org slash). The selected sequence may, where appropriate, be isolated directly by the use of appropriate restriction endonucleases, or more effectively by means of PCR amplification. Suitable techniques are described in, for example, U.S. Pat. Nos. 4,683,195, 4,683,202, 4,800,159, 4,965,188, as well as in Innis et al. eds., PCR Protocols: A guide to method and applications.

Following amplification and/or restriction endonuclease digestion, the desired gene or gene fragment is ligated either initially into a cloning vector, or directly into an expression vector that is appropriate for the chosen host cell type. In the case of the S. pneumoniae proteins, Escherichia coli is the most useful expression host. However, many other cell types may be also be usefully employed including other bacteria, yeast cells, insect cells and mammalian cell systems.

High-level expression of the desired protein within the host cell may be achieved in several different ways (depending on the chosen expression vector) including expression as a fusion protein (e.g. with factor Xa or thrombin), expression as a His-tagged protein, dual vector systems, expression systems leading to incorporation of the recombinant protein inside inclusion bodies etc. The recombinant protein will then need to be isolated from the cell membrane, interior, inclusion body or (in the case of secreted proteins) the culture medium, by one of the many methods known in the art.

All of the above recombinant DNA and protein purification techniques are well known to all skilled artisans in the field, the details of said techniques being described in many standard works including "Molecular cloning: a laboratory manual" by Sambrook, J., Fritsch, E. F. & Maniatis, T., Cold Spring Harbor, N.Y., $2^{nd}$ ed., 1989, which is incorporated herein by reference in its entirety.

As disclosed and explained hereinabove, each of the abovementioned embodiments of the invention may be based on the use of one or more intact, full length, cell wall and/or cell membrane proteins or, in the alternative, or in addition thereto, fragments, derivatives and modifications of said full length proteins. Fragments may be obtained by means of recombinant expression of selected regions of the cell wall protein gene(s). Alternatively, such fragments may be obtained by means of controlled, site-specific cleavage of the cell-wall proteins using one or more enzymes such as factor X, trypsin, chymotrypsin etc., as are well known in the art. Derivatives of the full length proteins or fragments thereof may be obtained by introducing non-native sequences within the DNA sequences encoding said proteins, followed by expression of said derivatized sequences. Derivatives may also be produced by conjugating non-native groups to the amino residue side chains of the cell wall proteins or protein fragments, using standard protein modification techniques. Modified cell wall proteins and protein fragments for use in the present invention may also be obtained by the use of site-directed mutagenesis techniques. Such techniques are well known in the art and are described, for example, in "Molecular cloning: a laboratory manual" by Sambrook, J., Fritsch, E. F. & Maniatis, T., Cold Spring Harbor, N.Y., $2^{nd}$ ed., 1989. Of particular interest is the use of one or more of the preceding techniques to create fragments or derivatives possessing the desired epitopic sites, but lacking other domains which are responsible for adverse effects such as suppression of cellular immune responses. It is to be emphasized that all of the immediately preceding discussion of fragments, derivatives and mutants of the cell wall proteins disclosed herein are to be considered as an integral part of the present invention.

The following examples are provided for illustrative purposes and in order to more particularly explain and describe the present invention. The present invention, however, is not limited to the particular embodiments disclosed in the examples.

EXAMPLE 1

Prevention of S. pneumoniae Infection in Mice by Inoculation with S. pneumoniae Cell Wall Protein Fractions Methods:

Bacterial Cells:

The bacterial strain used in this study was an S. pneumoniae serotype 3 strain. The bacteria were plated onto tryptic soy agar supplemented with 5% sheep erythrocytes and incubated for 17-18 hours at 37° C. under anaerobic conditions. The bacterial cells were then transferred to Todd-Hewitt broth supplemented with 0-5% yeast extract and grown to mid-late log phase. Bacteria were harvested and the pellets were stored at −70° C.

Purification of Cell Wall Proteins:

Bacterial pellets were resuspended in phosphate buffered saline (PBS). The resulting pellets were then treated with mutanolysin to release cell wall components. Supernatants containing the CW proteins were then harvested. Subsequently, the bacteria were sonicated and centrifuged and the resulting pellet containing the bacteria membranes (m) were lysed with 0.5% TRITON X-100 detergent.

Fractionation of the Cell Wall Protein Mixture:

Cell wall protein-containing supernatants were allowed to adhere to fetuin (a highly glycosylated pan-lectin binding protein) that was covalently bound to a sepharose column. Non-adherent molecules, obtained from the flow-through fraction were predominantly non-lectin molecules, while the column-adherent lectins were eluted with 50 mM ammonium acetate at pH 3.5.

Experimental: S. pneumoniae cell wall (CW) proteins were separated into lectin (CW-L) and non-lectin (NL) fractions by fetuin affinity chromatography, as described hereinabove. C57BL/6 and BALB/c mice were vaccinated with S. pneumoniae total CW (CW-T), CW-L and CW-NL protein preparations mixed with Freund's adjuvant, by means of the following procedure: each mouse was primed with 25 micrograms of CW-T, CW-NL and CW-L protein preparations intramuscularly, with complete Freund's adjuvant (CFA) and boosted with incomplete Freund's adjuvant (IFA), 4 and 7 weeks following priming. Western blots of the above-mentioned protein preparations were probed with sera obtained a week after the last immunization. Animals were then challenged intranasally (IN) or intraperitoneally (IP) with $10^8$ cfu of S. pneumoniae serotype 3, that caused 100% mortality in control mice immunized with CFA and boosted with IFA only within 96 hours post-inoculation. Vaccination with CW-L elicited partial protection against S. Pneumoniae IN and IP challenge (50% and 45% respectively). Vaccination with CW-T and CW-NL proteins elicited 70% and 65% protection against IP challenge, respectively. Vaccination with CW-T and CW-NL proteins elicited 85% and 50% protection against IN inoculation, respectively.

EXAMPLE 2

Determination of Age-related Immunoreactivity to S. pneumoniae Surface Proteins

The following study was carried out in order to investigate the age-related development of immunoreactivity to S. pneumoniae cell wall and cell membrane proteins.

Operating as described hereinabove in Example 1, a fraction containing cell wall proteins was obtained from a clinical isolate of S. pneumoniae. In addition, cell membrane proteins were recovered by solubilizing the membrane pellet (described hereinabove in Example 1) in 0.5% TRITON X-100 detergent. The cell wall and cell membrane proteins were separated by means of two-dimensional gel electrophoresis, wherein the proteins were separated using sodium dodecyl sulfate polyacrylamide gel electrophoresis (SDS-PAGE) in one dimension, and polyacrylamide gel isoelectric focusing in the other dimension.

The ability of serum prepared from blood samples of children aged 1.5, 2.5 and 3.5 years and adults to recognize the separated S. pneumoniae proteins was investigated by Western blot analysis according to the methods described by Rapola S. et al. [J. Infect. Dis. (2000) 182: 1146-52].

Putative identification of the separated protein spots obtained following the 2D-electrophoresis was achieved by the use of the Matrix Assisted Laser Desorption/Ionization mass spectrometery (MALDI-MS) technique.

Results of the above analysis are summarized in the following table:

| | | Age-dependent immunoreactivity to S. pneumoniae surface proteins(total, pH 4-6.5) | | | | |
|---|---|---|---|---|---|---|
| spot nr. | = x protein per spot | homology | age 1.5 | age 2.5 | age 3.5 | adult |
| 1 | 2 | DNA K/phosphoenolpyruvate protein phosphotransferase | * | * | * | * |
| 3 | 1 | trigger factor | * | * | * | * |
| 4 | 2 | 60 kDa chaperonin (proteinCPN60) (GroEL protein) elongation factor G/tetracycline resistance protein teto (TET(O)) | ** | * | ** | *** |
| 7 | 2 | Glutamyl-tRNA Amidotransferase subunit A/N utilization substance protein A homolog | * | ** | ? | *** |
| 11 | 2 | Oligopeptide-binding protein amiA/aliA/aliB precursor hypothetical zinc metalloproteinase in SCAA 5'region (ORF 6) | ? | ? | ? | ? |
| 12 | 1 | pneumolysin (thiol-activated cytolysin) | * | | * | ** |
| 13 | 1 | L-lactate dehydrogenase | * | ** | * | ? |
| 14 | 1 | Glyceraldehyde 3-phosphate dehydrogenase (GAPDH) | * | ** | *** | *** |
| 15 | 1 | fructose-biphosphate aldolase | ** | *** | *** | *** |
| 16 | 1 | UDP-glucose 4-epimerase | ** | * | ? | ? |
| 17 | 2 | elongation factor G/tetracycline resistance protein teto (TET(O)) gtp binding protein typA/BioA | * | ** | ? | ? |
| 18 | 1 | pyruvate oxidase | *** | *** | *** | *** |
| 22 | 1 | Glutamyl-tRNA synthetase | | * | ** | ? |
| 23 | 1 | NADP-specific glutamate dehydrogenase | * | | * | * |
| 24 | 1 | Glyceraldehyde 3-phosphate dehydrogenase (GAPDH) | * | ** | *** | **** |
| 25 | 1 | Enolase (2-phosphoglycerate dehydratase) | * | ** | ** | ** |
| 27 | 1 | phosphoglycerate kinase | * | ** | ** | ** |
| 29 | 1 | glucose-6-phosphate isomerase | | * | * | ** |

-continued

Age-dependent immunoreactivity to S. pneumoniae surface proteins(total, pH 4-6.5)

| spot nr. | = x protein per spot | homology | age 1.5 | age 2.5 | age 3.5 | adult |
|---|---|---|---|---|---|---|
| 30 | 2 | 40S ribosomal protein S1/6-phosphogluconate dehydrogenase | | | ? | ? |
| 31 | 1 | aminopeptidase C | | | ? | ? |
| new spots | | | | | | |
| 33 | | | | * | ** | *** |
| 55/62 | | | ** | *** | *** | *** |
| 57/65 | | | * | * | ** | ** |
| 58 | | | ** | * | ? | ? |

The data presented in the preceding table indicate that there is an age-dependent development of immunoreactivity to several S. pneumoniae cell wall and cell surface proteins.

EXAMPLE 3

Prevention of S. pneumoniae Infection in Mice by Inoculation with Recombinantly-expressed S. pneumoniae Cell Surface Proteins Cloning of Immunogenic S. pneumoniae Surface Proteins:

S. pneumoniae fructose-biphosphate aldolase (hereinafter referred to as "aldolase") and GAPDH proteins were cloned into the pHAT expression vector (Clontech) and expressed in E. coli BL21 cells (Promega Corp., USA) using standard laboratory procedures. Following lysis of the BL21 cells, recombinant proteins were purified by the use of immobilized metal affinity chromatography (IMAC) on Ni—NTa columns (Qiagen) and eluted with imidazole. In a separate set of experiments, S. pneumoniae aldolase cDNAs were cloned into the pVAC expression vector (Invivogen), a DNA vaccine vector specifically designed to stimulate a humoral immune response by intramuscular injection. Antigenic proteins are targeted and anchored to the cell surface by cloning the gene of interest in frame between the IL2 signal sequence and the C-terminal transmembrane anchoring domain of human placental alkaline phosphatase. The antigenic peptide produced on the surface of muscle cells is taken up by antigen presenting cells (APCs) and processed through the major histocompatibility complex (MHC) class II pathway.

Immunization:

BALB/c and C57BL/6 mice (7 week old females) were intramuscularly immunized with 25 micrograms of either recombinant aldolase or recombinant GAPDH proteins together with either Freund's complete adjuvant (CFA) or an alum adjuvant. In a separate set of experiments, mice of the aforementioned strains were intramuscularly immunized with 50 micrograms of the pVAC-aldolase or pVAC-GAPDH constructs that were described hereinabove.

Assessment of Immunogenicity:

The immunogenicity of recombinant S. pneumoniae aldolase and GAPDH proteins (1-2 micrograms of each one) was assessed by Western blot assay using serum of mice that had been immunized with either total cell wall proteins (CW-T) or with one of the recombinant proteins (as described hereinabove). The results obtained (FIG. 1) indicate that the sera of the immunized animals recognized both recombinant GAPDH and aldolase proteins, and the native GAPDH and aldolase proteins present in the CW-T mixture.

Figure 2:
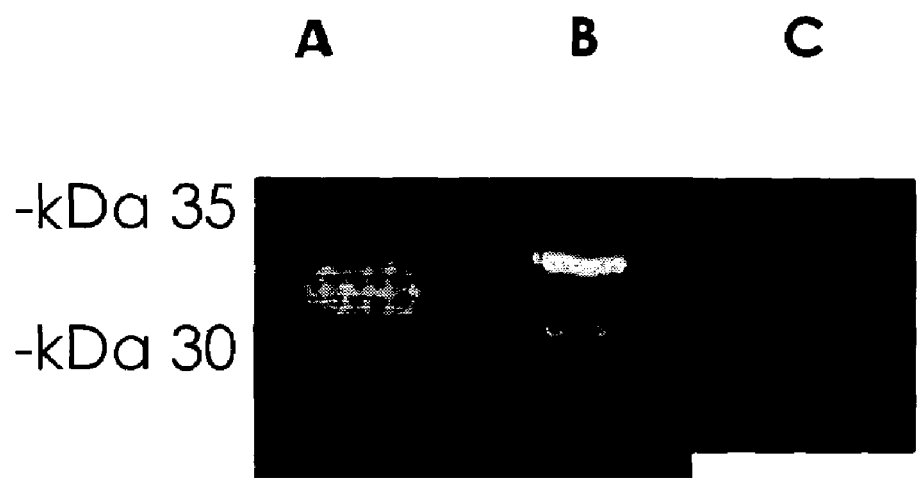
FIG. 2 is a photograph of a Western blot in which the sera of mice immunized with pVAC constructs containing the cDNA of S. pneumoniae fructose-biphosphate aldolase (A) and GAPDH (B) are seen to recognize the corresponding native proteins from electrophoretically-separated total cell wall protein preparation. Sera obtained following immunization with the pVAC parental plasmid did not recognize either of the two proteins (C).

In a separate set of experiments the serum of mice that had been immunized with the pVAC-aldolase or pVAC-GAPDH constructs, as described above, was used to detect native aldolase and GAPDH, respectively in Western blots obtained from SDS-PAGE separations of CW-T proteins. The results obtained (FIG. 2) indicate that inoculation with the pVAC-based constructs is capable of eliciting an immune response. Sera of mice vaccinated with the parental pVAC plasmid (i.e. without insert) did not, however, react with the CW-T proteins.

Figure 3:
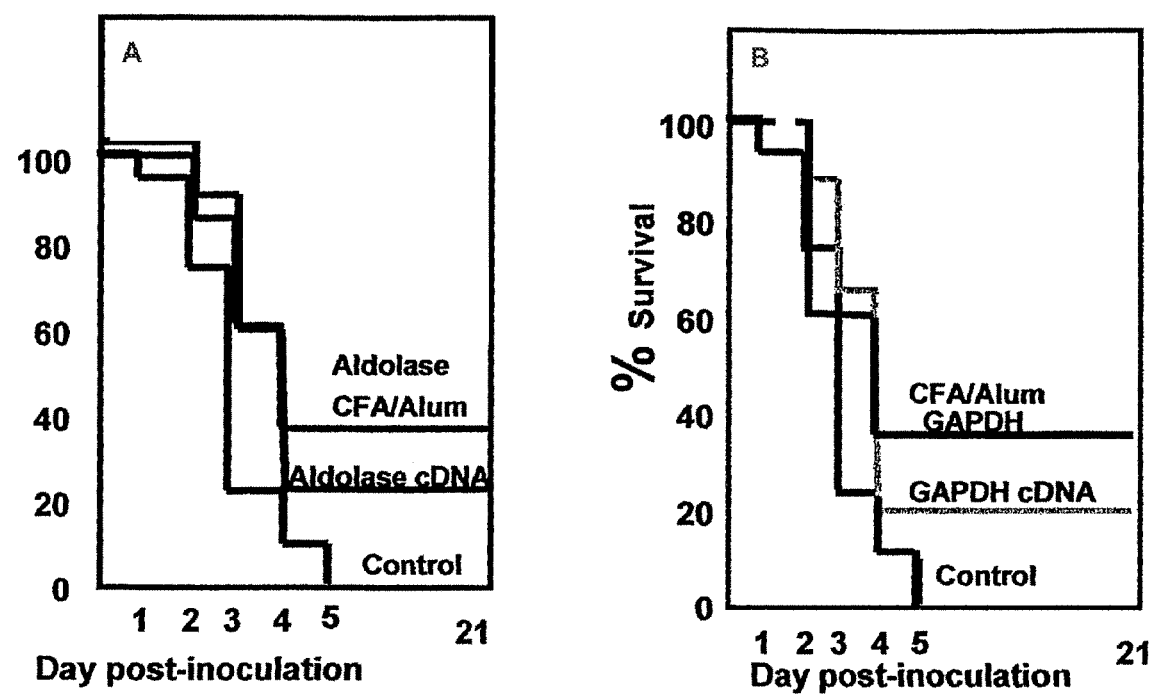
FIG. 3 is a graph describing the ability of recombinant fructose-biphosphate aldolase (FIG. 3A) and GAPDH (FIG. 3B) to elicit a protective immune response to intraperitoneal and intranasal challenge with a lethal dose of S. pneumoniae in the mouse model system.

Protective Vaccination:

Following immunization with the recombinant proteins as described hereinabove, the mice were challenged intranasally with a lethal dose of $10^8$ CFU of S. pneumoniae serotype 3. Only 10% of the control animals (immunization with either CFA or alum only) survived the bacterial challenge. However, 40% of the animals immunized with the recombinant aldolase protein in CFA and 43% of the animals immunized with the same protein in alum survived the challenge. Following immunization with the pVAC-aldolase construct, 33% of the animals survived as shown in FIG. 3A. With regard to recombinant GAPDH, 36% of the animals immunized with this recombinant protein (in either of the abovementioned adjuvants) survived. Immunization with the pVAC-GAPDH construct, led to a survival rate of 40% as shown in FIG. 3B.

EXAMPLE 4

S. pneumoniae Immunogenic Proteins

Operating essentially as in Example 2, the ability of serum prepared from blood samples of children aged 1.5, 2.5 and 3.5 years and adults to recognize the separated S. pneumoniae proteins was investigated by Western blot analysis according to the methods described by Rapola S. et al. [J. Infect. Dis. (2000) 182: 1146-52].

Identification of the separated protein spots obtained following the 2D-electrophoresis was achieved by the use of the Matrix Assisted Laser Desorption/Ionization mass spectrometry (MALDI-MS) technique, and comparison of the partial amino acid sequences obtained thereby with the sequences contained in the TIGR4 and/or R6 databases (maintained by The Institute for Genomic Research).

The cell surface proteins found to be immunogenic (classified according to their cellular location—cell membrane or cell wall) are summarized in the following table:

List of immunogenic proteins

| spot | | accession code from TIGR 4 or R6 |
|---|---|---|
| | cell wall proteins: homology to | |
| 1 | Phosphoenolpyruvate protein phosphotransferase | NP345645 |
| 2 | Probable phosphomannomutase | NP346006 |
| 3 | Trigger factor | NP344923 |
| 4 | Elongation factor G/tetracycline resistance protein teto (TET(O)) | NP344811/P72533 |
| 5 | DNA directed RNA polymerase alpha-chain | G95027 |
| 6 | NADH oxidase | NP345923 |
| 7 | Glutanryl-tRNA Amidotransferase subunit A | NP344960 |
| | N utilization substance protein A homolog. | P32727 |
| 8 | XAA-HIS dipeptidase | P45494 |
| | Cell division protein flsz. | NP346105 |
| 11 | Hypothetical zinc metalloproteinase in SCAA 5'region (ORF 6) | P42358 |
| 13 | L-lactate dehydrogenase | NP345686 |
| 14 | Glyceraldehyde 3-phosphate dehydrogenase (GAPDH) | NP346439 |
| 15 | Fructose-biphosphate aldolase | NP345117 |
| 16 | UDP-glucose 4-epimerase | NP346261 |
| | GTP binding protein typA/BipA | NP358192 |
| 21 | GMP synthase | NP345899 |
| 22 | Glutamyl-tRNA synthetase | NP346492 |
| 23 | NADP-specific glutamate dehydrogenase | NP345679 |
| 26 | Elongation factor TS | NP346622 |
| 27 | Phospboglycerate kinase | AAK74657 |
| 28 | Probable pyridine nucleotide-disulfide oxido-reductase | P77212 |
| 30 | 40S ribosomal protein SI | NP345350 |
| | 6-phosphogluconate dehydrogenase | NP357929 |
| 31 | Aminopeptidase C | NP344819 |
| 33 | Carbamoyl-phosphate synthase, large subunit | NP345739 |
| 57 | PTS system, mannose-specific IIAB components | NP344822 |
| 58 | Ribosoinal protein 32 | NP346623 |
| 62 | Dihydroorolate dehydrogenase | NP358460 |
| 65 | Aspartate carbamoyltransferase | NP345741 |
| | membrane proteins: homology to | |
| 14 | Elongation factor Tu | NP345941 |
| 19 | Pneumococcal surface Immunogenlc protein A (PsipA) | P344634 |
| 22 | Phosphoglycerate kinase | NP358035 |
| 40 | ABC transporter, substrate-binding protein | NP344690 |
| | lectins: homology to | |
| 10 | Endopeptidase O | NP346087 |
| 14 | Pneumococcal surface Immunogenic protein B (PsipB) | NP358083 |
| | Pneumococcal surface Immunogenic protein C (PsipC) | NP345081 |

EXAMPLE 5

Preparation of an *S. pneumoniae* Fructose Biphosphate Aldolase Fragment

A peptide referred to as ALDO 1, corresponding to the first 294 nucleotides of the coding sequence of the fructose biphosphate aldolase gene (SP0605 *Streptococcus pneumoniae* TIGR4) (see SEQ ID NO:1 of the sequence listing that forms an integral part of the present disclosure), was amplified from *S. pneumoniae* strain R6 genomic DNA by means of PCR with the following primers:

```
Forward
(5'- GGT ACC ATG GCA ATC GTT TCA GCA-3',
                                    SEQ ID NO:2)

Reverse
(5'- GAG CTC ACC AAC TTC GAT ACA CTC AAG-3',
                                    SEQ ID NO:3).
```

Figure 4:
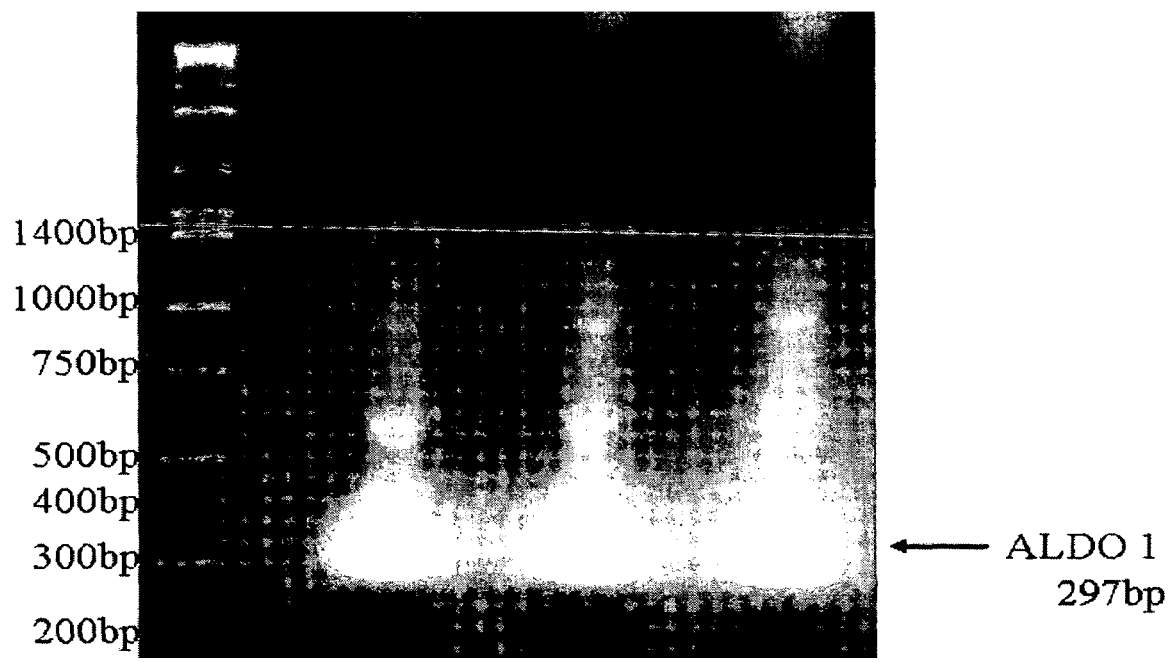
FIG. 4 is a photograph of a gel depicting the 297 base pair ALDO 1-containing fragment of S. pneumoniae fructose biphosphate aldolase.

The amplified product obtained thereby is shown in FIG. 4.

Figure 5A:
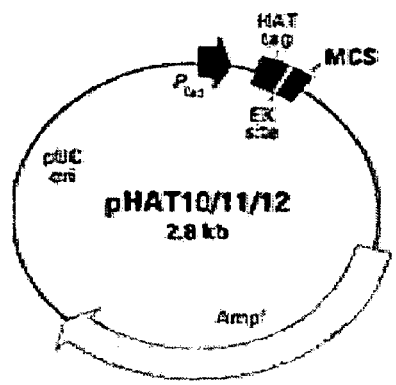
Figure 5B:
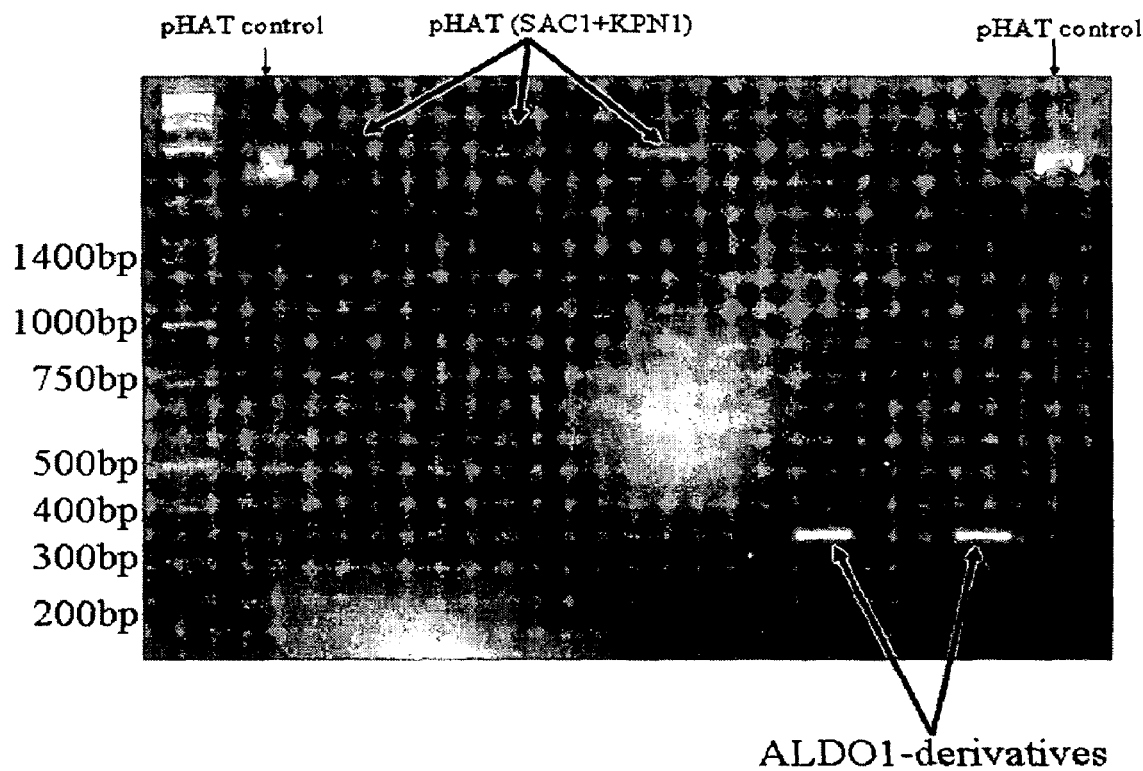
FIG. 5B depicts an agarose gel separation of ALDO 1 and the pHAT vector after restriction by Kpn1 and SacI enzymes.

The Forward and Reverse primers contain Kpn1 and SacI recognition sequences, respectively. The primers flank the entire open reading frames. The amplified and Kpn1-SacI (Takara Bio Inc, Shiga, Japan) digested DNA-fragments were cloned into the pHAT expression vector (BD Biosciences Clontech, Palo Alto, Calif., USA), as illustrated in FIGS. 5A and 5B and transformed in DH5a ULTRAMAX ultracompetent *E. coil* cells.

Figure 6:
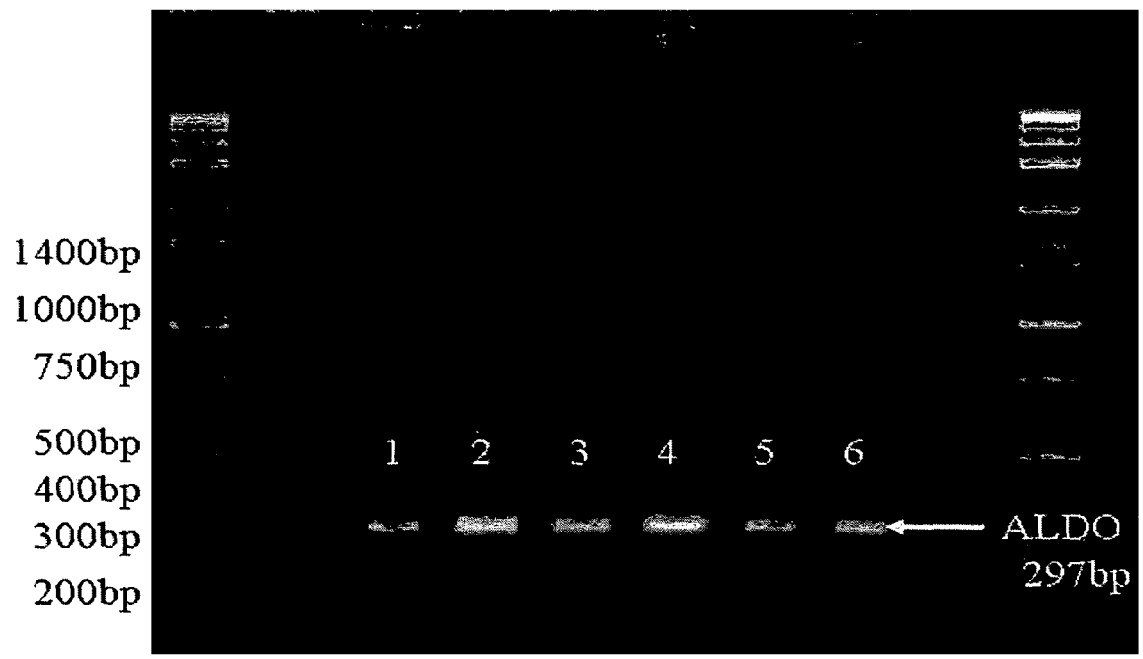
FIG. 6 is a photograph of an agarose gel showing the 297 bp PCR amplification product (comprising ALDO 1) obtained from colonies transformed with the pHAT/ALDO 1 construct.

Ampicillin-resistant transformants were cultured and plasmid DNA was analyzed by PCR. The pHAT-ALDO 1 vector was purified from DH5α ULTRAMAX cells using the Qiagen High Speed Plasmid Maxi Kit (Qiagen GMBH, Hilden, Germany) and transformed in *E. coil* host expression strain BL21(DE3)pLysS. PCR amplification of the ALDO 1 fragment from transformed positive colonies yielded the 297 bp fragment indicated in the gel shown in FIG. 6.

While specific embodiments of the invention have been described for the purpose of illustration, it will be understood that the invention may be carried out in practice by skilled persons with many modifications, variations and adaptations, without departing from its spirit or exceeding the bounds of the present invention.

The invention claimed is:

1. A vaccine composition comprising an isolated immunogenically active fragment of *Streptococcus pneumoniae* fructose-biphosphate aldolase, wherein the fragment consists of the amino acid sequence encoded by the first 294 nucleotides of the coding sequence of said *Streptococcus pneumoniae* fructose-biphosphate aldolase as set forth in SEQ ID NO: 1.

2. The vaccine composition of claim 1, wherein the composition comprises one or more additives.

3. The vaccine composition of claim 2, wherein the additive is an adjuvant.

4. A method of vaccinating a mammalian subject comprising administering to said subject the vaccine composition of claim 1.

5. A method of vaccinating a mammalian subject comprising administering to said subject the vaccine composition of claim 2.

6. A method of vaccinating a mammalian subject comprising administering to said subject the vaccine composition of claim 3.

* * * * *

```
                              SEQUENCE LISTING

<160> NUMBER OF SEQ ID NOS: 1

<210> SEQ ID NO 1
<211> LENGTH: 294
<212> TYPE: DNA
<213> ORGANISM: Streptococcus pneumoniae

<400> SEQUENCE: 1
atggcaatcg tttcagcaga aaaatttgtc caagcagccc gtgacaacgg ttatgcagtt      60
ggtggattta acacaaacaa ccttgagtgg actcaagcta tcttgcgcgc agcagaagct     120
aaaaaagctc cagttttgat ccaaacttca atgggtgctg ctaaatacat gggtggttac     180
aaagttgctc gcaacttgat cgctaacctt gttgaatcaa tgggtatcac tgtaccagta     240
gctatccacc ttgaccacgg tcactacgaa gatgcacttg agtgtatcga agtt           294
```